US00PP07984P

United States Patent [19]

Stravers

[11] Patent Number: Plant 7,984

[45] Date of Patent: Sep. 22, 1992

[54] GERBERA PLANT NAMED TERIKATIR

[75] Inventor: Lambertus J. M. Stravers, Kudelstaart, Netherlands

[73] Assignee: Terra Nigra BV, PA De Kwakel, Netherlands

[21] Appl. No.: 645,602

[22] Filed: Jan. 25, 1991

[51] Int. Cl.[5] ..... A01H 5/00

[52] U.S. Cl. ..... Plt./68.1

[58] Field of Search ..... Plt./68

*Primary Examiner*—James R. Feyrer

*Attorney, Agent, or Firm*—Foley & Lardner

[57] ABSTRACT

A new and distinct cultivar of Gerbera plant named Terikatir, characterized by its semi-double flower type and flat flower form, yellow ray floret color, yellow perianth lobes, dark purple disc, and 60–69 mm overall flower diameter.

1 Drawing Sheet

The present invention comprises a new and distinct cultivar of Gerbera, botanically known as *Gerbera jamesonii*, and referred to by the cultivar name Terikatir.

Terikatir was originated by applicant from a hybridization made in a controlled breeding program in De Kwakel, The Netherlands in 1988.

The female parent was a cultivar identified as 87.442. The male parent was a cultivar identified as M88.330. The new cultivar was discovered and selected by applicant as one flowering plant within the progeny of the stated parentage in or about January 1989 in a controlled environment in De Kwakel.

The first asexual reproduction of Terikatir was accomplished when vegetative cuttings were taken from the initial selection in April 1989 in a controlled environment in De Kwakel, The Netherlands. Horticultural examination of selected units initiated in November 1989 has demonstrated that the combination of characteristics as herein disclosed for Terikatir are firmly fixed and are retained through successive generations of asexual reproduction. Terikatir is presently being propagated by cuttings and by tissue culture.

Terikatir has not been observed under all possible environmental conditions. The phenotype may vary significantly with variations in environment such as temperature, light intensity and day length. The following observations, measurements and comparisons describe plants grown in the greenhouses of Terra Nigra BV in De Kwakel, The Netherlands under controlled conditions which closely approximate those generally used in commercial practice.

The following traits have been repeatedly observed and have been determined to be basic characteristics of Terikatir, which in combination distinguish this Gerbera as a new and distinct cultivar:

1. Semi-double flower type.
2. Flat flower form.
3. Yellow ray floret color.
4. Yellow perianth lobes.
5. Dark purple disc.
6. Overall flower diameter of 60–69 mm.

Of the many commercial cultivars known to the present inventor, there is none which can be meaningfully compared to Terikatir and its unique characteristics.

The accompanying photographic drawing shows typical inflorescence characteristics of Terikatir, with the colors being as nearly true as possible with illustrations of this type. The photograph comprises a closeup view of the flower form and color of the new cultivar.

In the following description, color references are made to The Royal Horticultural Society Colour Chart (RHS). The color values were determined at approximately 12:00 noon on Nov. 9, 1990 under artificial light at De Kwakel, The Netherlands.

Classification:

*Botanical.*—*Gerbera jamesonii* cv Terikatir.

*Commercial.*—Gerbera.

Parentage: Seedling from cross of 87.442 and M88.330.

Plant: The plant when fully grown reaches a height of 40 cm.

Leaf blade:

*Length.*—Short, 35–40 cm.

*Width.*—Narrow, 15 cm.

*Thickness.*—Medium.

*Blistering (puckering).*—Medium.

*Pubescence on upper side.*—Sparse (midrib excluded).

*Depth of cuts or incisions in leaf.*—Near bottom or base: Strong. Near middle: Medium. Near tip: Weak.

*Color.*—Upper surface of leaf, medium green 137A; lower surface, light green.

*Glossiness on upper side.*—Weak.

*Angle of apex.*—Right angle.

*Shape of apex.*—Pointed.

*Margin of lobes.*—Serrate.

*Petiole length.*—Medium, 10 cm.

*Extension of margin.*—Absent.

*Petiole anthocyanin coloration.*—Present, medium in intensity.

Peduncle:

*Length.*—Medium, 60 cm.

*Cross section.*—Round, medium thickness and strong.

*Tendency to fascination.*—Absent.

*Pubescence.*—Medium.

*Color.*—Medium green.

*Anthocyanin.*—Present, medium in intensity, none present at tip.

*Bracts near tip.*—Absent.

Flower head:

*Type.*—Semi-double with dark purple center; generally flat shaped in form.

*Diameter from edge to edge.*—60–69 mm.

*Height.*—From point of attachment of involucre to top of flower head is medium, 22 mm.

*Involucre.*—Height: Medium, 15 mm. Diameter: Small, 30 mm. Number of bracts: 52; longitudinal axis on inner rows is straight. Anthocyanin: Present at top of inner involucral bracts. Pubescence: Weak.

*Outer row ray florets.*—Number in outer row: 40–60. Length of floret: Under 29 mm. Width of floret: 5–9 mm. Shape of floret: Longitudinal folding is medium. Cross section of floret: Flat. Length of free petals: Under 29 mm. Color distribution on inner side: Uniform; edge if similar in color. Striation: Absent. Claw spot: Absent. Color on top side: 21B. Color on bottom side: 15C. Angle of apex: Obtuse. Shape of apex:

Rounded. Incisions of apex: Present, two in number, shallow in depth.

*Disc florets.*—Diameter: 10–19 mm. Main color of perianth lobes: Yellow for both male and female flowers. Color (mature and immature): Dark purple.

Reproductive parts:

*Stigma.*—Main color, yellow.

*Anthers.*—Main color. Yellow; color at top lighter relative to other parts. Longitudinal striping: Present.

*Pappus.*—Main color: Yellow; color of top relative to other parts is darker. Orientation: Level of top relative to closed disc florets is the same.

I claim:

1. A new and distinct cultivar of Gerbera plant named Terikatir, as illustrated and described.

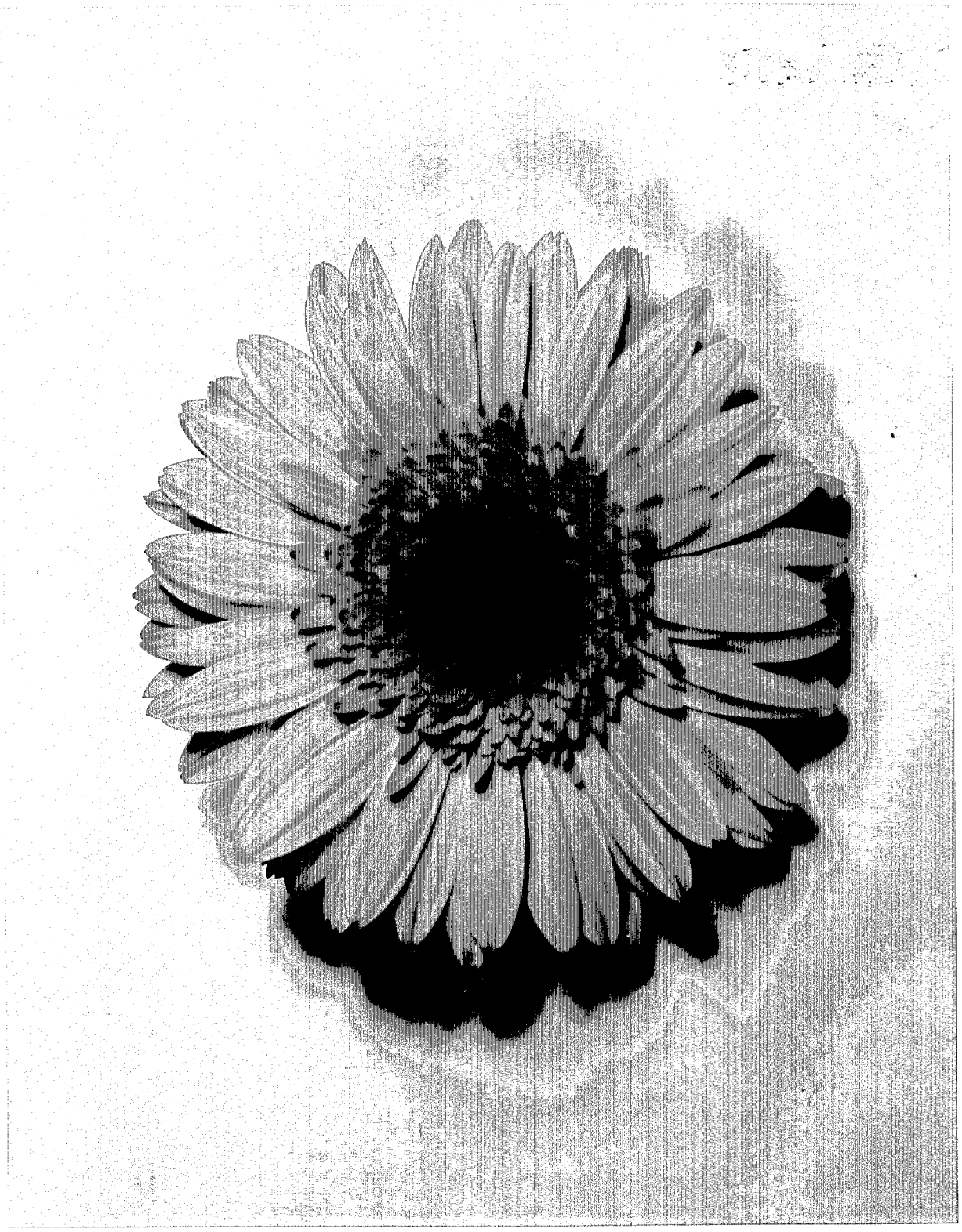

* * * * *